(12) United States Patent
Tanaka et al.

(10) Patent No.: US 6,579,990 B2
(45) Date of Patent: Jun. 17, 2003

(54) PROCESS FOR PRODUCING REFINED PYROMELLITIC ACID AND REFINED PYROMELLITIC ANHYDRIDE

(75) Inventors: Kazuo Tanaka, Kurashiki (JP); Atsushi Okoshi, Kurashiki (JP); Kengi Nakaya, Kurashiki (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 09/933,075

(22) Filed: Aug. 21, 2001

(65) Prior Publication Data

US 2002/0049339 A1 Apr. 25, 2002

(30) Foreign Application Priority Data

Aug. 23, 2000 (JP) .......................... 2000-252405
Aug. 23, 2000 (JP) .......................... 2000-252406

(51) Int. Cl.$^7$ .................. C07D 493/00; C07C 51/42
(52) U.S. Cl. ...................... 549/239; 562/486
(58) Field of Search ................ 562/494, 887, 562/888, 898, 486; 549/231, 236, 239

(56) References Cited

U.S. PATENT DOCUMENTS

| | | | |
|---|---|---|---|
| 4,014,755 A | * | 3/1977 | Richter .................... 203/73 |
| 4,694,089 A | * | 9/1987 | Kosaka et al. ............. 549/239 |
| 4,906,760 A | * | 3/1990 | Mueller et al. ............ 549/239 |
| 5,041,633 A | * | 8/1991 | Partenheimer et al. ...... 562/413 |

FOREIGN PATENT DOCUMENTS

| | | |
|---|---|---|
| FR | 2 134 513 | 12/1972 |
| FR | 2 134 514 | 12/1972 |
| JP | 62-59280 | 3/1987 |

OTHER PUBLICATIONS

Aldrich Catalog Handbook of Fine Chemicals, Sigma–Aldrich Co., USA (1988), p. 36.*

* cited by examiner

Primary Examiner—Richard L. Raymond
Assistant Examiner—Zachary C. Tucker
(74) Attorney, Agent, or Firm—Armstrong, Westerman & Hattori, LLP

(57) ABSTRACT

A process for refined pyromellitic anhydride which comprises dissolving crude pyromellitic acid or crude pyromellitic anhydride in water, then cooling an aqueous solution thus obtained to perform crystallization as pyromellitic acid, then separating a crystal thus obtained from water, then anhydrating the crystal of pyromellitic acid thus separated with heating to produce pyromellitic anhydride, then vaporizing pyromellitic anhydride thus produced, cooling vapor of pyromellitic anhydride thus obtained, and thereby, recovering a refined crystal of pyromellitic anhydride.

8 Claims, No Drawings

PROCESS FOR PRODUCING REFINED PYROMELLITIC ACID AND REFINED PYROMELLITIC ANHYDRIDE

BACKGROUND OF THE INVENTION

1) Field of the Invention

The present invention relates to a process for producing refined pyromellitic acid to be used as a raw material of coating agent, etc., and a process for producing refined pyromellitic anhydride to be used as a raw material of polyimide resins with high heat resistance, cross-linking agents for foam polyester and particular plasticizers.

2) Prior Art

As processes for producing pyromellitic acid, a process for producing pyromellitic acid by liquid phase oxidation of durene and a process for producing pyromellitic acid by liquid phase oxidation of 2,4,5-trimethyl benzaldehyde have been known. As a process for producing pyromellitic anhydride by dehydration refining of crude pyromellitic acid, a process comprising dehydrating crude pyromellitic acid in the presence of aliphatic acid anhydride such as acetic anhydride has been known. However, the above-mentioned process possesses a defect of a high cost since acetic anhydride is used.

Further, as a process for producing pyromellitic anhydride, a process comprising performing gas phase of durene or 2,4,5-trimethyl benzaldehyde has been known.

Japanese Patent Kokai (Laid-open) No.62-59280 discloses a process for producing pyromellitic anhydride comprising heating pyromellitic acid at a specific temperature.

Pyromellitic acid and pyromellitic anhydride produced by the above-mentioned processes contain a small amount of by-products such as trimellitic acid (TMA) and methyl trimellitic acid (MTMA) and have been often colored. Although Japanese Patent Kokai (Laid-open) No.62-59280 discloses to dehydrate pyromellitic acid recystallized with water, pyromellitic anhydride thus obtained is a little colored. Therefore, further a high quality of pyromellitic anhydride and pyromellitic acid has been required.

SUMMARY OF THE INVENTION

An object of the present invention is to provide a process for producing refined pyromellitic acid and refined pyromellitic anhydride which little contain by-products and are not colored.

As a result of extensive studies to solve the above-mentioned prior art problems, the inventors have found that a high quality of refined pyromellitic acid with a large particle diameter not to be colored can be produced with an industrial advantage by dissolving colored crude pyromellitic acid or crude pyromellitic anhydride containing by-products with heating in water and then cooling an aqueous solution thus obtained to perform crystallization as pyromellitic acid, then separating a crystal thus obtained to obtain pyromellitic acid little containing impurities, then heat dehydrating pyromellitic acid thus obtained, then vaporizing pyromellitic anhydride thus obtained, cooling the vapor and recovering a refined crystal of pyromellitic anhydride and furthermore pyromellitic acid not to be colored, little containing impurities can be obtained by dissolving crude pyromellitic acid or crude pyromellitic anhydride with heating in water, performing contact treatment of an aqueous solution thus obtained with activated carbon, then separating the aqueous solution from activated carbon, then cooling the aqueous solution to perform crystallization as pyromellitic acid and separating the crystal, and a refined pyromellitic anhydride can be readily produced by heat dehydrating pyromellitic acid thus obtained at a temperature of 170 to 260° C., and have accomplished the present invention.

That is, the present invention provides a process for refined pyromellitic anhydride which comprises:

dissolving crude pyromellitic acid or crude pyromellitic anhydride in water, then, cooling an aqueous solution thus obtained to perform crystallization as pyromellitic acid, then, separating a crystal thus obtained from water, then, anhydrating the crystal of pyromellitic acid thus separated with heating to produce pyromellitic anhydride, then, vaporizing pyromellitic anhydride thus produced, cooling vapor of pyromellitic anhydride thus obtained, and thereby, recovering a refined crystal of pyromellitic anhydride.

Further, the present invention provides a process for producing refined pyromellitic acid which comprises:

dissolving crude pyromellitic acid or crude pyromellitic anhydride in water, then, performing a contact treatment of an aqueous solution thus obtained with activated carbon, then separating the aqueous solution from activated carbon, then, cooling the aqueous solution to perform crystallization as pyromellitic acid, then, separating a crystal thus obtained from water, and thereby, recovering refined pyromellitic acid.

The present invention provides a process for producing refined pyromellitic anhydride which comprises:

dissolving crude pyromellitic acid or crude pyromellitic anhydride in water, then, performing a contact treatment of an aqueous solution thus obtained with activated carbon, then separating the aqueous solution from activated carbon, then, cooling the aqueous solution to perform crystallization as pyromellitic acid, then, separating a crystal thus obtained from water to recover refined pyromellitic acid, and dehydrating pyromellitic acid thus recovered with heating at a temperature of 170 to 260° C. to obtain refined pyromellitic anhydride, or further vaporizing pyromellitic anhydride thus produced, cooling vapor of pyromellitic anhydride thus obtained, and thereby, recovering a refined crystal of pyromellitic anhydride.

DETAILED DESCRIPTION OF THE INVENTION

The present invention will be described in detail below.

As the refining raw materials in the present invention, crude pyromellitic acid obtained by liquid phase oxidation of durene or 2,4,5-trimethyl benzaldehyde, crude pyromellitic anhydride obtained by gas phase oxidation of durene or 2,4,5-trimethyl benzaldehyde or anhydride of crude pyromellitic acid obtained by the above-mentioned liquid phase oxidation can be used. Particularly, crude pyromellitic acid obtained by liquid phase oxidation of 2,4,5-trimethyl benzaldehyde is preferable as the refining raw material.

As water to dissolve crude pyromellitic acid or crude pyromellitic anhydride, ion-exchanged water or distilled water is used. The weight ratio of water to crude pyromellitic acid or crude pyromellitic anhydride is 2/1 to 10/1 and preferably 3/1 to 8/1. Minimum amount of water necessary to dissolve crude pyromellitic acid or crude pyromellitic anhydride is preferable since too large amount of water lowers the yield.

The dissolving temperature is in the range of 70 to 180° C. and preferably 80 to 160° C.

The crystallization is performed by cooling an aqueous solution dissolved a refining raw material. Any method for cooling including natural cooling such as cooling under standing at ambient temperature, cooling applied boiling heat removal by reflux under a reduced pressure and exterior cooling used a medium such as water may be applied. Particularly, cooling under a reduced pressure is preferable. The cooling velocity is suitably decided depending on a crystal size of intended pyromellitic acid. It is preferable that final crystallization temperature is in the range of 20 to 40° C. As the process for crystallization, a batch process or continuous process can be applied.

The crystal thus formed is separated from water by suitable means such as filtration, decantation and centrifugal separation. The separation apparatus can be selected properly from a sedimentation concentrator, a liquid cyclone a centrifugal separator, a super decanter, a vacuum filter and an applied pressure filter. If necessary, adhered mother liquid may be removed with water washing. A refined pyromellitic acid can be obtained by drying a crystal thus obtained. In this procedure of crystallization, a major portion of trimellitic acid and methyl trimellitic acid as impurities is transferred to the mother liquid phase, whereby refined pyromellitic acid is obtained as a crystal.

In order to obtain refined pyromellitic acid which is little colored, it is preferable that crude pyromellitic acid or crude pyromellitic anhydride is dissolved in water and then contact treatment of an aqueous solution thus obtained with activated carbon is performed and then cooling for crystallization of pyromellitic acid is performed.

The temperature to perform contact treatment of the aqueous solution of dissolved crude pyromellitic acid or crude pyromellitic anhydride with activated carbon is in the range of 70 to 180 ° C. and preferably 80 to 160 ° C. It is preferable that the dissolving temperature is the same as the activated carbon contact treatment temperature.

As the activated carbon, granular or powdery coconut hush type activated carbon or coal type and liquid phase type activated carbon is used. Activated carbon with decoloring potency is preferable. Example of activated carbon includes trade names "Kurarecoal GLC, GL", obtainable on the market, manufactured by Kurare Chemical k.k., in Japan and "Fuji Activated carbon" obtainable on the market, manufactured by Daisan Kogyo k.k., in Japan.

The activated carbon contact treatment of the aqueous solution of crude pyromellitic acid or crude pyromellitic anhydride can be performed in a batch process, a semi-batch process or a continuous process. It is preferable that an amount of activated carbon is 1 to 30 parts by weight per 100 parts by weight of crude pyromellitic acid or crude pyromellitic anhydride. When the contact treatment is performed in a continuous process, a fixed bed or a suspension bed can be applied. It is preferable that the activated carbon contact treatment time (contact time) is in the range of 0.2 to 10 hours.

Activated carbon and absorbed impurities can be readily removed by suitable means such as filtration and decantation.

The crystallization for the aqueous dissolution solution subjected to activated carbon contact treatment is performed by cooling. In this crystallization, conditions of crystallization, a process for crystallization and a process for separation of a crystal thus formed are the same as in the above-mentioned case of not performing activated carbon contact treatment.

Refined pyromellitic acid is heat dehydrated at a temperature of 170 to 260 ° C. and preferably 180 to 240° C., whereby pyromellitic anhydride is obtained. When the heating temperature is below 170° C., the dehydration efficiency is low, whereas above 260° C. there is a fear that pyromellitic anhydride is colored. The heating time is 1 to 20 hours and preferably 3 to 10 hours.

As the apparatus for heat dehydration of pyromellitic acid, any type apparatuses including a fluid bed, a fixed bed, a batch type, a semi-continuous type and a continuous type may be applied on the condition that a solid can be uniformly heated.

As the pressure in heat dehydration, atmospheric pressure, an applied pressure or a reduced pressure can be applied. Atmospheric pressure or a reduced pressure is preferable, considering simplicity of apparatus and discharge efficiency of water.

The pyromellitic anhydride thus obtained is vaporized and then cooled, whereby refined crystal of pyromellitic anhydride is recovered.

When the above-mentioned activated carbon contact treatment is not performed in the production of refined pyromellitic acid, the vaporization treatment is particularly effective in the production of refined pyromellitic anhydride which is little colored.

The vaporizing pressure is a reduced pressure of 150 Torr or below and preferably 120 Torr or below. The vaporizing temperature is in the range of 250 to 400° C. The melting point of pyromellitic anhydride is 287° C. The vaporization operation of pyromelitic anhydride in a liquid state is preferable since handling in a liquid state is easier than in a solid state and pyromellitic anhydride in a liquid state can be readily fed continuously to a refining apparatus. The vaporization of pyromellitic anhydride is performed preferably in the condition of 290 to 350° C.

The cooling temperature of pyromellitic anhydride vapor is usually 200° C. or below and preferably 100° C. or below. It is preferable that cooling is performed at a gas phase portion in an apparatus to vaporize pyromellitic anhydride by heating under a reduced pressure or at a cooling portion with a plate form cooling surface connected to the above-mentioned gas phase portion. The crystal of pyromellitic anhydride adhered to a plate form cooling surface can be readily recovered with a scratching apparatus.

It is preferable that the time necessary for vaporization is short in order to reduce thermal decomposition as much as possible. The time is usually in the range of 0.2 to 8 hours and preferably in the range of 0.5 to 5. When the time is above 8 hours, trimellitic anhydride is produced, so that the purity of pyromellitic anhydride is decreased.

Any process including a batch process, a semi-continuous process and a continuous process can be applied to vaporization, cooling and recovery of pyromellitic anhydride.

PREFERRED EMBODIMENT OF THE INVENTION

The present invention will be described in more detail below, referring to Examples and Comparative Examples, which are not intended to limit the scope of the present invention.

The colored degree of pyromellitic anhydride in the below Examples was represented by methanol dissolution color. The methanol dissolution color was determined by the following method.

5 g of a sample was dissolved in 100 ml of methanol. An absorbance of a solution thus obtained at a wave length of 430 nm was measured. 100 times of measured value was indicated as methanol dissolution color.

REFERENCE EXAMPLE (Production of Crude Pyromellitic Acid)

A catalyst liquid of bromine ion concentration 2.3% by weight (hereinafter "wt %"), manganese ion concentration 0.44 wt % and iron ion concentration 13 ppm, mixed 1450.3 g of water, 15.3 g of 100% hydrogen bromide, 34.4 g of manganese bromide (tetrahydrate) and 0.1 g of ferric bromide was charged to a first stage reactor of a continuous two stage type reactor connected two Zr autoclaves of inner capacity 2L, provided with a reflux condenser, a stirrer, a heater, a raw material transfer port, a gas introducing port and a reaction product withdrawing port and 1000 g of the same catalyst liquid as in the first stage reactor was charged to the second stage reactor. Nitrogen was introduced thereto under an applied pressure from the gas introducing port to elevate the pressure to 1 MPa and the temperature was elevated up to 220° C. with the heater. Then 2,4,5-trimethyl benzaldehyde at the rate of 90 g/hr and the catalyst liquid at the rate of 780 g/hr with the same components as in the charge liquid to the reactor each separately were fed to the first stage reactor. Introduction of air was started from the gas introducing port simultaneously with feeding of 2,4,5-trimethyl benzaldehyde and a flow rate of air was controlled so as to maintain the oxygen concentration in an exhaust gas from the reactor to 2.5%. Then, transference of the liquid from the first stage reactor to the second stage reactor was started while maintaining the liquid level in the first stage reactor to a constant level and simultaneously the catalyst liquid of bromine concentration 3.3 wt % mixed 58 g of water and 2 g of 100% hydrogen bromide was fed at the rate of 60 g/hr to the second stage reactor and introduction of air was started from the gas introducing port and a flow rate of air was controlled so as to maintain the oxygen concentration in an exhaust gas from the reactor to 4.5%. 1150 g/hr of the reaction product was withdrawn from the second stage reactor while maintaining the liquid level in the second stage reactor to a constant level. Meantime, the pressure in the reactors was maintained to the first stage; 3.2 MPa and the second stage; 2.9 MPa.

The reaction product liquid thus obtained was hydrogenated at 150° C. under 1 MPa in the presence of a 0.5% Pd/C catalyst and cooled. Then, a crystal thus obtained was separated by filtration and dried, whereby crude pyromellitic acid was obtained. Crude pyromellitic acid thus obtained contained trimellitic acid 1.6 wt % and methyl trimellitic acid 0.97 wt % and its purity was 96.7 wt %.

COMPARATIVE EXAMPLE 1

300 g of crude pyromellitic acid obtained in Reference Example was dissolved in 2200 g of pure water at 80° C. and maintained in the state for 0.5 hour and then cooled to perform crystallization. Then, a crystal thus obtained was separated from water at 40° C. and then rinsed with an equal amount of water and dried at 120° C. over one day.

200 g of pyromellitic acid thus dried was heated at 250° C. for 10 hours with stirring to perform dehydration. The measured results of purity and properties of pyromellitic acid and pyromellitic anhydride thus obtained were shown in Table 1.

EXAMPLE 1

The same treatment as in Comparative Example 1 was performed. 150 g of pyromellitic anhydride thus obtained was simple distilled in 70 Torr at 305° C. The distillation time was one hour. The recovery percentage of pyromellitic anhydride was 95%. The measured results of properties of pyromellitic anhydride thus obtained were shown in Table 1.

EXAMPLE 2

The treatment was performed in the same manner as in Example 1 except that pyromellitic anhydride was simple distilled in 50 Torr at 297° C. The distillation time was one hour. The recovery percentage of pyromellitic anhydride was 90%. The measured results of properties of pyromellitic anhydride thus obtained were shown in Table 1.

COMPARATIVE EXAMPLE 2

200 g of crude pyromellitic acid obtained in Reference Example was heat dehydrated at 250° C. for 10 hours with stirring without performing crystallization and rinsing. 150 g of pyromellitic anhydride thus obtained was simple distilled in 70 Torr at 305° C. The distillation time was one hour. The recovery percentage of pyromellitic anhydride was 95%. The measured results of purity and properties of pyromellitic acid and pyromellitic anhydride thus obtained were shown in Table 1.

As clear from Examples 1 and 2, according to the process of the present invention, a high quality of refined pyromellitic anhydride which little contains by-products and is not colored can be produced by dissolving crude pyromellitic acid or crude pyromellitic anhydride in pure water and cooling an aqueous solution thus obtained to perform crystallization as pyromellitic acid and then heat dehydrating pyromellitic acid thus obtained and then distilling pyromellitic anhydride thus obtained.

EXAMPLE 3

300 g of crude pyromellitic acid obtained in Reference Example and 50 g of activated carbon, trade name "Kurarecoal GL" (10 to 30 mesh), obtained on the market, manufactured by Kurare Chemical k.k., in Japan were added to 2200 g of pure water and dissolved at 80° C. and maintained in the state for 0.5 hour and then cooled to perform crystallization. Then a crystal thus obtained was separated from water at 40° C. and then rinsed with an equal amount of water and dried at 120° C. over one day, whereby refined pyromellitic acid was obtained.

200 g of refined pyromellitic acid thus obtained was heated at 250° C. for 10 hours with stirring to perform dehydration, whereby refined pyromellitic anhydride was obtained. The measured results of purity and properties of refined pyromellitic acid and refined pyromellitic anhydride thus obtained were shown in Table 2.

EXAMPLE 4

The treatment was performed in the same manner as in Example 3 except that activated carbon, trade name "Kurarecoal GLC" (10 to 30 mesh), obtained on the market, manufactured by Kurare Chemical k.k., in Japan was used instead of activated carbon, trade name "Kurarecoal GL". The measured results of purity and properties of refined pyromellitic acid and refined pyromellitic anhydride thus obtained were shown in Table 2.

COMPARATIVE EXAMPLE 3

The treatment was performed in the same manner as in Example 3 except that no activated carbon contact treatment was performed. The measured of purity and properties of pyromellitic acid and pyromellitic anhydride thus obtained were shown in Table 2.

As clear from Examples 3 and 4, according to the process of the present invention, a high quality of refined pyromellitic acid which little contains by-products and is not colored can be produced by dissolving crude pyromellitic acid or crude pyromellitic anhydride in pure water and performing activated carbon contact treatment of an aqueous solution thus obtained and then separating the aqueous solution from activated carbon and then cooling the aqueous solution to perform crystallization as pyromellitic acid and furthermore refined pyromellitic anhydride which little contains by-products and is not colored can be produced by heat dehydrating refined pyromellitic anhydride thus obtained.

The present invention is industrially significant since the process of the present invention is an excellent process in which a high quality of refined pyromellitic acid and refined pyromellitic anhydride can be readily produced.

TABLE 1

|  | Pyromellitic acid | | | | Pyromellitic anhydride | | |
| --- | --- | --- | --- | --- | --- | --- | --- |
|  | Purity (wt %) | Trimellitic acid (wt %) | Methyl trimellitic acid (wt %) | Methanol dissolution color | Trimellitic acid (wt %) | Methyl trimellitic acid (wt %) | Methanol dissolution color |
| Example 1 | 99.6 | 0.11 | 0.18 | 1.0 | 0.04 | 0.08 | 0.7 |
| 2 | 99.6 | 0.11 | 0.18 | 1.0 | 0.04 | 0.07 | 0.7 |
| Comp. Ex. 1 | 99.6 | 0.11 | 0.18 | 1.0 | 0.07 | 0.09 | 13.5 |
| 2 | 96.7 | 1.60 | 0.97 | light yellow | 1.00 | 0.48 | 0.9 |

TABLE 2

|  | Pyromellitic acid | | | | Pyromellitic anhydride | | |
| --- | --- | --- | --- | --- | --- | --- | --- |
|  | Purity (wt %) | Trimellitic acid (wt %) | Methyl trimellitic acid (wt %) | Methanol dissolution color | Trimellitic acid (wt %) | Methyl trimellitic acid (wt %) | Methanol dissolution color |
| Example 3 | 99.6 | 0.11 | 0.18 | 0.2 | 0.07 | 0.15 | 2.7 |
| 4 | 99.6 | 0.11 | 0.18 | 0.2 | 0.07 | 0.15 | 1.8 |
| Comp. Ex. 3 | 99.6 | 0.11 | 0.18 | 1.0 | 0.07 | 0.15 | 13.5 |
| R.r.m ※ | 96.7 | 1.60 | 0.97 | light yellow | — | — | — |

Note ※: Refining raw material (crude pyromellitic acid)

What is claimed is:

1. A process for producing refined pyromellitic anhydride which comprises:
   dissolving crude pyromellitic acid containing trimellitic acid and methyl trimellitic acid by-products in water,
   then, cooling an aqueous solution thus obtained to perform crystallization as pyromellitic acid,
   then, separating a crystal thus obtained from water,
   then, anhydrating the crystal of pyromellitic acid thus separated with heating using no solvent to produce pyromellitic anhydride,
   after the completion of anhydration, distilling pyromellitic anhydride thus produced in a one-stage process under a reduced pressure of 150 Torr or below at a temperature of 250 to 400° C.,
   cooling vapor of pyromellitic anhydride thus obtained, and
   thereby, recovering a refined crystal of pyromellitic anhydride having a lower content of trimellitic acid and methyl trimellitic acid by-products than the crude pyromellitic acid.

2. The process according to claim 1, wherein a ratio of water to crude pyromellitic acid is 2/1 to 10/1.

3. The process according to claim 1, dissolving crude pyromellitic acid in water at a temperature of 70 to 180° C.

4. The process according to claim 1, cooling the solution under a reduced pressure to perform crystallization as pyromellitic acid.

5. The process according to claim 1, separating the crystal of pyromellitic acid from water by filtration, decantation or centrifugal separation.

6. The process according to claim 1, anhydrating the crystal of pyromellitic acid with heating at a temperature of 170 to 260° C.

7. The process for producing refined pyromellitic anhydride which comprises:
   dissolving crude pyromellitic acid containing trimellitic acid and methyl trimellitic acid by-products in water,
   then, performing a contact treatment of an aqueous solution thus obtained with activated carbon,
   then, separating the aqueous solution from activated carbon,
   then, cooling the aqueous solution to perform crystallization as pyromellitic acid,
   then, separating a crystal thus obtained from water,
   then, anhydrating the crystal of pyromellitic acid thus separated with heating using no solvent to produce pryomellitic anhydride,
   after the completion of anhydration, distilling pyromellitic anhydride thus produced in a one stage process under a reduced pressure of 150 Torr or below at a temperature 250 to 400° C.,
   cooling vapor of pyromellitic anhydride thus obtained, and
   thereby, recovering a refined crystal of pyromellitic anhydride having a lower content of trimellitic acid and methyl trimellitic acid by-products than the crude pyromellitic acid.

8. The process according to claim 7, cooling the aqueous solution under a reduced pressure to perform crystallization as pyromellitic acid.

* * * * *